United States Patent
Li et al.

(10) Patent No.: US 9,828,412 B2
(45) Date of Patent: Nov. 28, 2017

(54) SHORT PEPTIDE TARGETING EPS8 BINDING WITH EGFR AND USE THEREOF

(71) Applicant: SOUTHERN MEDICAL UNIVERSITY, Guangzhou (CN)

(72) Inventors: Yu Hua Li, Guangzhou (CN); Tong Yuan Xue, Guangzhou (CN)

(73) Assignee: SOUTHERN MEDICAL UNIVERSITY, Guangzhou, Guangdong (CN)

( * ) Notice: Subject to any disclaimer, the term of this patent is extended or adjusted under 35 U.S.C. 154(b) by 0 days.

(21) Appl. No.: 14/758,955

(22) PCT Filed: Dec. 25, 2014

(86) PCT No.: PCT/CN2014/094896
§ 371 (c)(1),
(2) Date: Jul. 1, 2015

(87) PCT Pub. No.: WO2015/172563
PCT Pub. Date: Nov. 19, 2015

(65) Prior Publication Data
US 2016/0145302 A1   May 26, 2016

(30) Foreign Application Priority Data
May 14, 2014 (CN) .......................... 2014 1 0203873

(51) Int. Cl.
*A61K 38/00* (2006.01)
*C07K 7/06* (2006.01)
(52) U.S. Cl.
CPC ............... *C07K 7/06* (2013.01); *A61K 38/00* (2013.01)

(58) Field of Classification Search
None
See application file for complete search history.

(56) References Cited

PUBLICATIONS

Cheng He et al., "The Epidermal Growth Factor Receptor Juxtamembrane Domain Has Multiple Basolateral Plasma Membrane Localization Determinants, Including a Dominant Signal with a Polyproline Core", J. Biol. Chem., vol. 277, No. 41, Oct. 11, 2002; pp. 38284-38293.
Yu-Hua Li et al., "Novel Oncoprotein EPS8: A New Target for Anticancer Therapy", Future Oncol. 2013, vol. 9, No. 10, pp. 1587-1594.
Natalia Jura et al., "Mechanism for Activation of the EGF Receptor Catalytic Domain by the Juxtamembrane Segment", Cell, No. 137, Jun. 26, 2009, pp. 1293-1307.
Francesca Fazioli et al., "EPS 8 A Substrate for the Epidermal Growth Factor Receptor Kinase, Enhances, EGF-Dependent Mitogenic Signals" The EMBO Journal, 1993, vol. 12 No. 10, pp. 3799-3808.

*Primary Examiner* — Jeanette Lieb
(74) *Attorney, Agent, or Firm* — Novick, Kim & Lee, PLLC; Allen Xue

(57) ABSTRACT

The present invention discloses a short peptide targeting EPS8 binding with EGFR and use thereof, and sequence of the short peptide is N'-Arg-Lys-Lys-Asn-Lys-Pro-Pro-Pro-Pro-Lys-Lys-C'. The short peptide can effectively inhibit proliferation of EPS8 positive tumors, and can also be used to make a pharmaceutical preparation for treating EPS8 positive tumors, which has the potential of being developed into anti-cancer peptide inhibitor drugs.

11 Claims, 7 Drawing Sheets

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: synthesized

<400> SEQUENCE: 1

Arg Lys Lys Asn Lys Pro Pro Pro Pro Lys Lys
1               5                   10
```

SHORT PEPTIDE TARGETING EPS8 BINDING WITH EGFR AND USE THEREOF

FIELD OF INVENTION

The invention belongs to the research fields in pharmaceutical chemistry and peptides biotechnology, in particular to a short peptide targeting EPS8 binding with EGFR and use thereof.

BACKGROUND OF THE INVENTION

Epidermal Growth Factor Receptor pathway substrate No. 8 (EPS8) is phosphorylation substrate of multiple receptor and non-receptor tyrosine kinases, first discovered by Fazioli et al. in Epidermal Growth Factor Receptor (EGFR), signaling pathways of mice fibroblast NIH3T3. Recent studies showed that EPS8 is unusually overexpressed in tissues and cells of various solid tumors (e.g. cervical cancer; colorectal cancer, pituitary tumor, oral squamous cell carcinoma, pancreatic ductal cancer, breast cancer, thyroid cancer, esophageal cancer and glioblastoma, etc.) and hematological malignancies (e.g. multiple myeloma, lymphoma, acute myeloid leukemia, mixed lineage leukemia or acute lymphoid leukemia), whereas lower or not expressed in normal tissues and cells. Further studies showed that EPS8 promotes tumor cell proliferation by regulating cell cycle, facilitates tumor cell metastasis by participating in cell pseudopodia formation and interacting with actin, and correlates with patient prognosis by influencing tumor cell resistance against chemotherapeutic drug (Li Y*, Xue T He Y, Du J. Novel oncoprotein EPS8: a new target for anticancer therapy [J] Future Oncology, 2013 October; 9 (10): 1587-94.). Therefore, EPS8 has become a new target in monitoring and treatment of the tumor, and provides a brand new road for tumor targeting therapy.

Among the inhibitors targeting different structural domains of EGFR, such as Herceptin (Herceptin, trastuzumab) targeting extracellular domain and Gefitinib (Iressa, gefitinib) targeting at kinase domain, most of them possess shortcomings in poor specificity, drug resistance, and severe side-effects, albeit their clinical application has achieved encouraging efficacy. Therefore, it is imperative that much safer, more effective, and more specific anti-cancer drugs are developed to meet the urgent needs in clinical practice. However, unlike the other growth factor receptors, the juxtamembrane domain of EGFR plays an "activating" rather than "self-restricting" role towards kinase domain (Jura N et al. Mechanism for activation of the EGF receptor catalytic domain by the juxtamembrane segment [J] Cell, 2009, 137 (7):1293-1307). Novel inhibitors targeting juxtamembrane domain possess better specificity and selectivity, which provide a novel target for malignant tumor diseases. Compared with above small molecular inhibitors, peptide inhibitors own a variety of merits, such as higher activity, lower dose, less toxicity, and amino acids as end-product of drug metabolism, which have already become a hot topic in therapy targeting tumors.

SUMMARY OF INVENTION

To solve above problems, the present invention provides a short peptide targeting EPS8 binding with EGFR and use thereof.

To achieve above goals, the present invention adopts following technical scheme:

A short peptide targeting EPS8 binding with EGFR, the sequence of which is SEQ ID NO: 1 N'-Arg-Lys-Lys-Asn-Lys-Pro-Pro-Pro-Pro-Lys-Lys-C'.

Preferably, the carboxyl of Lysine in C' terminus of the short peptide of SEQ ID NO: 1 is amidated: N' Arg-Lys-Lys-Asn-Lys-Pro-Pro-Pro-Pro-Lys-Lys-$NH_2$-C'.

Preferably, the short peptide blocks interaction between EPS8 and EGFR.

A drug treating EPS8 positive tumors, the active ingredient is the short peptide.

Preferably, the ingredients of the drug also include pharmaceutically applicable excipients.

Preferably, the forms of the drug consist of injection, tablet, capsule, aerosol suppository, film, controlled or sustained release agent or nano formulation.

Use of the short peptide to make a pharmaceutical preparation for treating EPS8 positive tumors.

Preferably, the EPS8 positive tumors include cervical cancer, colorectal cancer, pituitary tumor, oral squamous cell carcinoma, pancreatic ductal cancer, breast cancer, thyroid cancer, esophageal cancer, glioblastoma, multiple myeloma, lymphoma, acute myeloid leukemia, mixed lineage leukemia, or acute lymphoid leukemia.

By using Computer Aided Drug Design (CADD) technology, the inventors successfully designed a short peptide targeting EPS8 binding with EGFR, named it P01, and further discovered that it completely docked to the juxtamembrane region of EGFR (FIG. 1, $L^{664}$-$I^{682}$). Therefore, the inventors synthesized short peptide P01, detected its anti-proliferation activity against EPS8 overexpression tumor cell lines KG1α (human acute myeloid leukemia cell line) and MCF-7 (human breast cancer cell line) by MTS assay, and preliminarily acquired cell viability line graphs of KG1α cells and MCF-7 cells (FIGS. 5 & 6). Furthermore, the inventors labeled P01 with FITC, observed its transmembrane effect with inverted fluorescence microscopy and laser scanning confocal microscopy, and confirmed it successfully penetrated KG1α cells (FIGS. 7 & 8).

Compared with available techniques, the present invention possesses the following benefits:

(1) Short peptide P01 can effectively inhibit proliferation of EPS8 positive tumors, and possesses the potential of being developed into novel anti-cancer peptide inhibitor drugs.

(2) Short peptide P01 targets EPS8, functions towards the juxtamembrane region of EGFR, and possesses better specificity and selectivity.

(3) Compared with small molecular inhibitors, short peptide P01, as a novel member of peptide inhibitors, owns a variety of merits, such as higher activity, lower dose, less toxicity, and amino acids as end-product of drug metabolism.

DETAILED DESCRIPTION OF THE PREFERRED EMBODIMENTS

The inventors describe the present invention with the following examples and figures. These examples are merely used for description rather than as restricting the scope of the present invention. Methods and reagents in the present invention all belong to available techniques, thus will not be explained here.

Example 1 Peptide Synthesis

Figure 1:
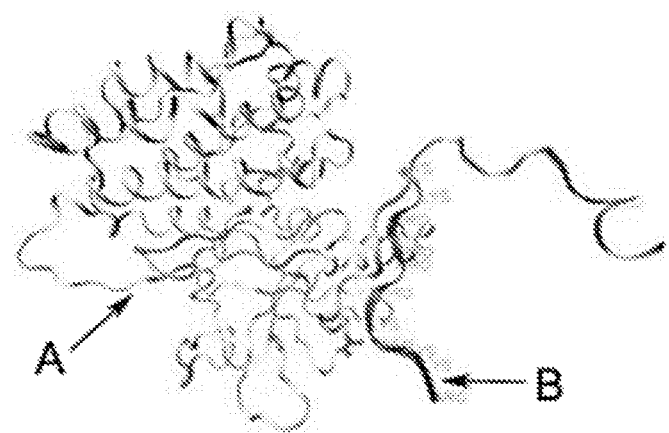
FIG. 1 shows the conformation schematic of molecular docking between the present invention short peptide P01 and EGFR. Arrow A indicates EGFR. Arrow B indicates P01.
Figure 2:
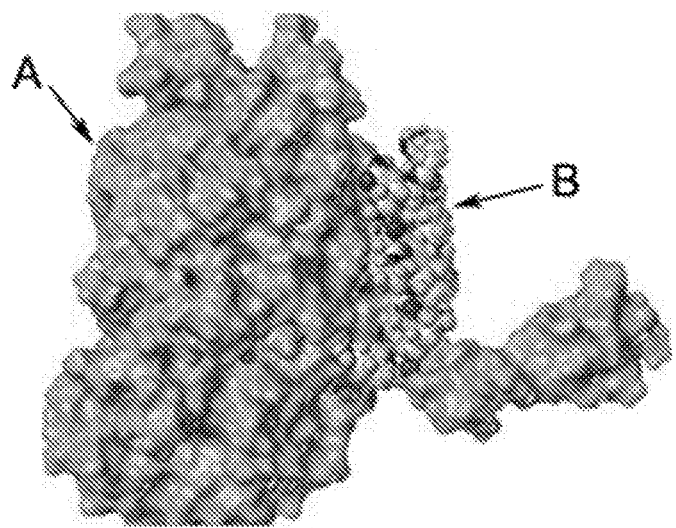
FIG. 2 shows the three-dimensional structure schematic of molecular docking between the present invention short peptide P01 and EGFR. Arrow A indicates EGFR. Arrow B indicates P01.

By CADD technology, the inventors successfully designed a short peptide targeting EPS8 binding with EGFR, and named it P01. Therefore, the sequence of short peptide P01 is illustrated in SEQ ID NO: 1: N'-Arg-Lys-Lys-Asn-Lys-Pro-Pro-Pro-Pro-Lys-Lys-C'. Then by conformation analysis, it was discovered that P01 completely docked to the juxtamembrane domain of EGFR (FIGS. 1 & 2, $L^{664}$-$I^{682}$). This was consistent with the fact that the interaction between EPS8 and EGFR is mainly mediated by electrostatic force between six acidic amino acids, Glu, in the juxtamembrane region of receptor and basic amino acids, Arg, Lys and His, in the head and tail regions of ligand (Fazioli F et al Eps8, a substrate for the epidermal growth factor receptor kinase, enhances EGF-dependent mitogenic signals [J]. EMBO J, 1993, 12(10):3799-3808.).

Figure 3:
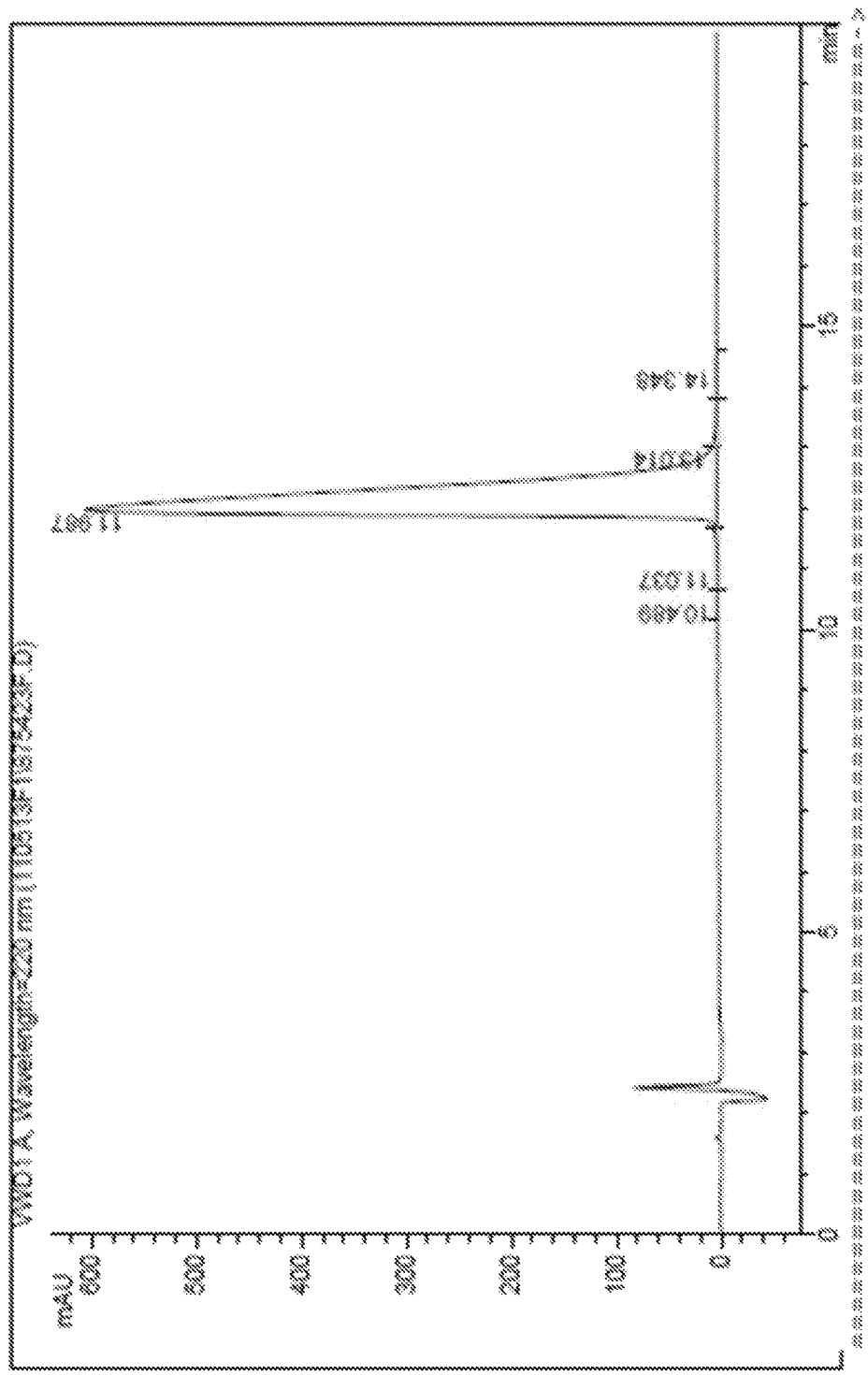
FIG. 3 shows the HPLC spectrum of the present invention short peptide P01.
Figure 4:
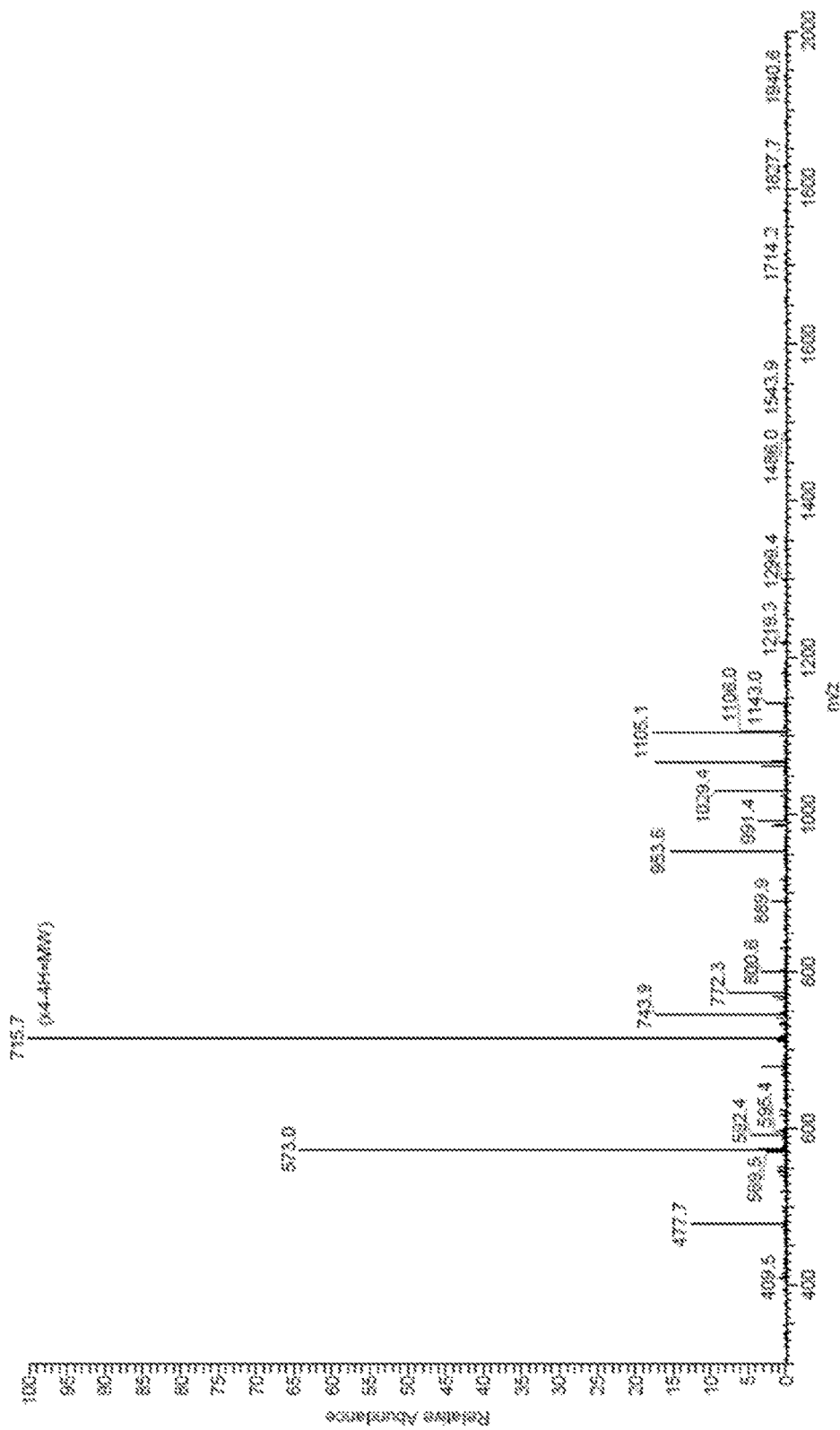
FIG. 4 shows the MS spectrum of the present invention short peptide P01.

Short peptide P01 synthesis was commissioned by the Chinese Peptide Company with Fmoc standard protocol. The carboxyl of Lys in C' terminus was amidated to protect Lys, and the sequence of P01 was SEQ ID NO: 1, N'-Arg-Lys-Lys-Asn-Lys-Pro-Pro-Pro-Pro-Lys-Lys-NH$_2$-C'. By reversed-phase high-performance liquid chromatography (HPLC) method, the inventors purified P01, and analyzed its purity. Then the inventors identified P01 and detected its molecular weight by mass spectrometry (MS) method. The purity of P01 was 98.9% (FIG. 3), and the molecular weight of P01 was 2858.5 (FIG. 4), which were consistent with theoretical values.

The acquired P01 was then dissolved in dimethyl sulfoxide (DMSO) to make stock solution, stored at −70° C., and diluted with phosphate buffered saline (PBS) prior to use.

Example 2 Anti-Proliferation Activity of Short Peptide P01 Against EPS8 Overexpression Tumor Cell Line—KG1α

EPS8 overexpression tumor cell line KG1α (human acute myeloid leukemia cell line, purchased from the American Type Culture Collection, ATCC) were selected as target cells, and seeded in 96-well plates at 10,000 cells/well and 100 μL/well. The medium culture was Roswell Park Memorial Institute (RPMI)-1640 containing 10% fetal bovine serum (FBS). 8 hours later, short peptide P01 was added at the different final concentrations of 0, 100, 300 and 500 μg/mL. KG1α cells were incubated with short peptide P01 for 24 hours, 48 hours and 72 hours. Then OD values at the wavelength of 490 nm were detected by MTS assay, and KG1α cell viability was calculated.

Figure 5:
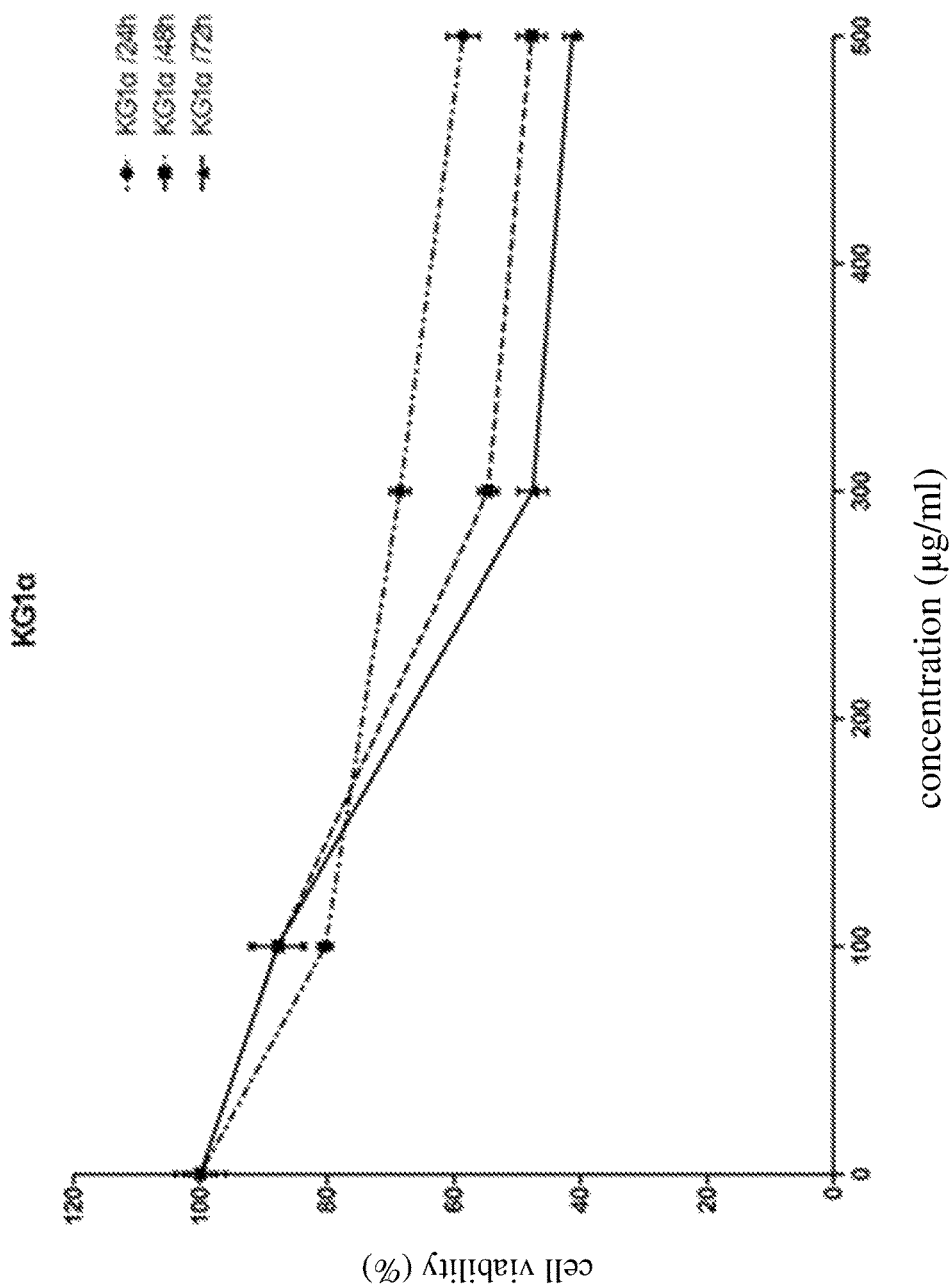
FIG. 5 shows the cell viability line graphs of EPS8 overexpression tumor cell line—KG1α incubated with short peptide P01 according to Example 2.

KG1α cell viability=[(OD$_{experimental}$-OD$_{blank\ control}$)]/[(OD$_{negative\ control}$-OD$_{blank\ control}$)]×100%. Cell viability line graphs of KG1α cells incubated with short peptide P01 were illustrated in FIG. 5: at 24 hours, IC$_{50}$ was 888.5 μg/mL (95% CI: 810.4 μg/mL~974.1 μg/mL); at 48 hours, IC$_{50}$ was 413.9 μg/mL (95% CI: 389.3 μg/mL~444.0 μg/mL); at 72 hours, IC$_{50}$ was 335.6 μg/mL (95% CI: 316.1 μg/mL~356.2 μg/mL).

Therefore, the short peptide P01 showed best anti-proliferation activity at 335.6 μg/mL for 72 hours, thus possessing the potency of being developed into new anti-cancer peptide inhibitor drugs.

Example 3 Anti-Proliferation Activity of Short Peptide P01 Against EPS8 Overexpression Tumor Cell Line MCF-7

EPS8 overexpression tumor cell line MCF-7 (human breast cancer cell line, purchased from ATCC) were selected as target cells, and seeded in 96-well plates at 10,000 cells/well and 100 μL/well. The medium culture was Dulbecco's Modified Eagle's Medium (DMEM) containing 10% FBS. 8 hours later, short peptide P01 was added at different final concentration of 0, 100, 300 and 500 μg/mL. MCF-7 cells were incubated with short peptide P01 for 24 hours, 48 hours and 72 hours. Then OD values at wavelength of 490 nm were detected by MTS assay, and MCF-7 cell viability was calculated.

Figure 6:
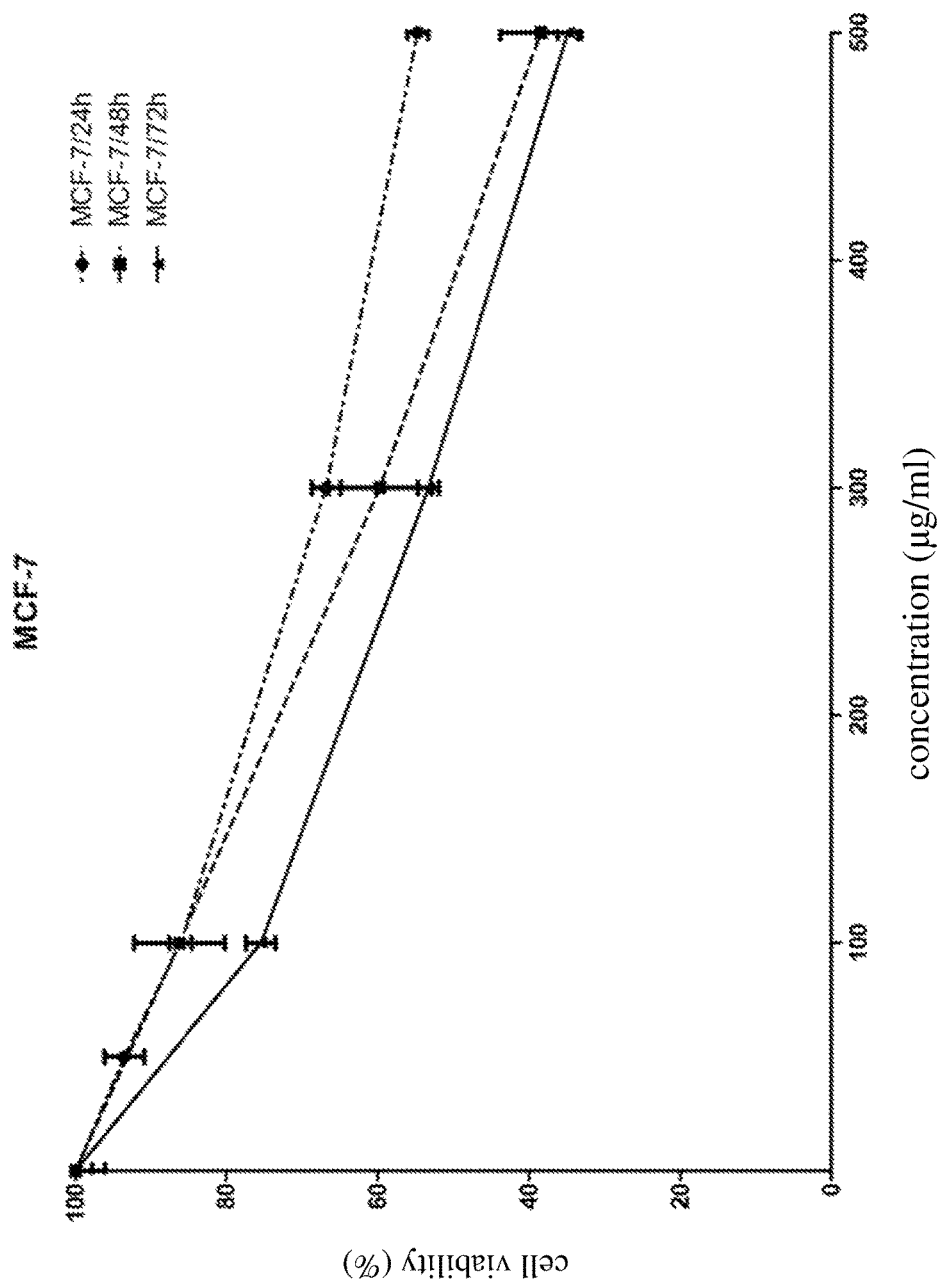
FIG. 6 shows the cell viability line graphs of EPS8 overexpression tumor cell line—MCF-7 incubated with short peptide P01 according to Example 3.

MCF-7 cell viability=[(OD$_{experimental}$-OD$_{blank\ control}$)]/[(OD$_{negative\ control}$-OD$_{blank\ control}$)]×100%. Cell viability line graphs of MCF-7 cells incubated with short peptide P01 are illustrated in FIG. 6: at 24 hours, IC$_{50}$ was 594.2 μg/mL (95% CI: 572.5 μg/mL~616.8 μg/mL); at 48 hours, IC$_{50}$ was 374.9 μg/mL (95% CI: 352.9 μg/mL~398.3 μg/mL); at 72 hours, IC$_{50}$ was 304.7 μg/mL (95% CI: 294.7 μg/mL~315.1 μg/mL).

Therefore, the short peptide P01 showed best anti-proliferation activity at 304.7 μg/mL for 72 hours, thus possessing the potential of being developed into a new anti-cancer peptide inhibitor drugs.

Example 4 Use of Short Peptide P01 and Application in Novel Drugs Treating EPS8 Positive Tumors The present invention also provides application of short peptide P01 as development into new drugs treating EPS8 positive tumors. The active ingredient of the drug is short peptide P01, and the ingredients also include pharmaceutically-applicable excipients, which referred to conventional pharmaceutical carriers, e.g. release agents and excipients such as water; fillers such as starch and sucrose; binders such as cellulose derivatives, alginates, gelatin and polyvinyl pyrrolidone; humectants such as glycerol; disintegrating agents such as agar, calcium carbonate, and sodium bicarbonate; absorption accelerators such as quaternary ammonium compounds; surfactants such as cetyl alcohol; adsorption carriers such as kaolin and bentonite; lubricants such as talc, calcium/magnesium stearate, and polyethylene glycol. In addition, the drug may also be added with other adjuvants, such as flavoring agents and sweeteners. The forms of the drug consist of injection, tablet, capsule, aerosol, suppository, film, controlled or sustained release agent or nano formulation.

"EPS8 positive tumors" in the present invention includes, whereas not limited to, cervical cancer, colorectal cancer, pituitary tumor, oral squamous cell carcinoma, pancreatic ductal cancer, breast cancer, thyroid cancer, esophageal cancer, glioblastoma, multiple myeloma, lymphoma, acute myeloid leukemia, mixed lineage leukemia, or acute lymphoid leukemia.

Figure 7:
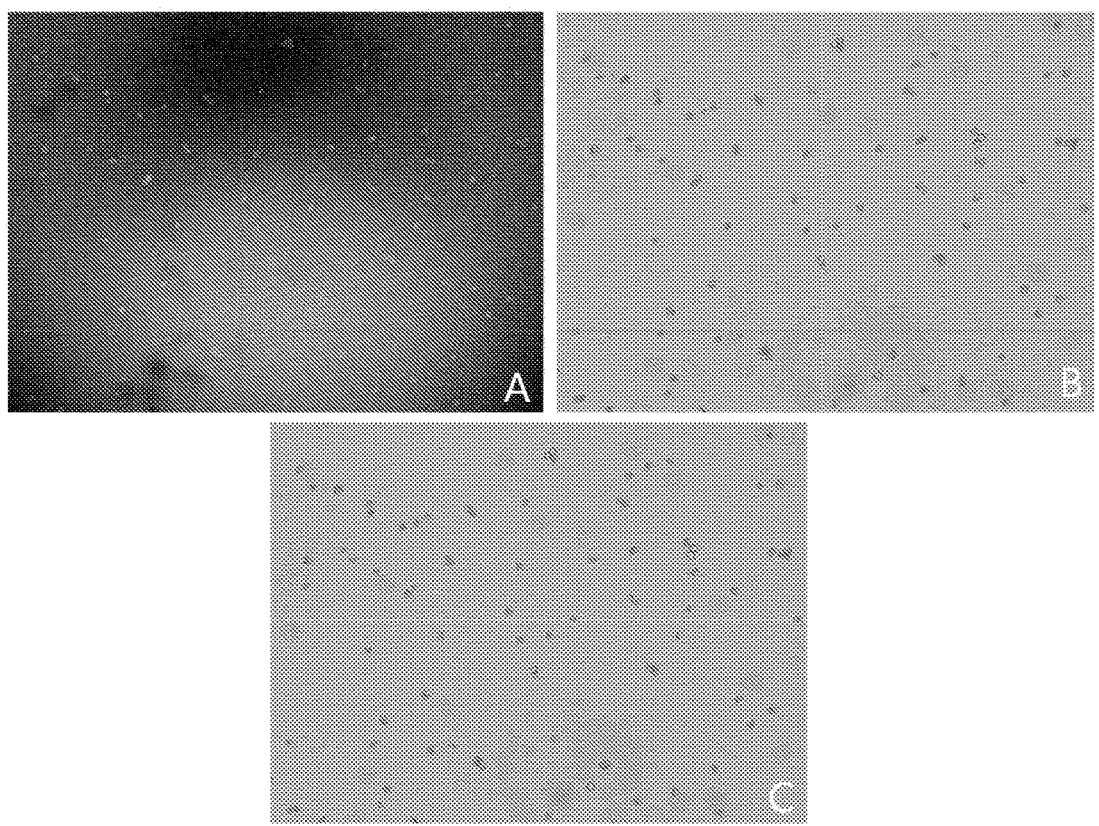
FIG. 7 shows the transmembrane effect of FITC-labeled P01 with inverted fluorescence microscope at different wavelengths according to Example 5. (A) 488 nm; (B) overlay of 488 nm and blank control; (C) blank control.

Example 5 Transmembrane Effect of FITC-Labeled Short Peptide P01 with Inverted Fluorescence Microscopy KG1α cells were seeded in 6-well plates at $2\times10^5$ cells/well and 1 mL/well. The medium culture was RPMI-1640 containing 10% FBS. 8 hours later, FITC-labeled short peptide P01 was added at final concentration of 2000 μg/mL. 24 hours later, transmembrane effect of FITC-labeled short peptide P01 was observed with inverted fluorescence microscopy (FIG. 7). Compared with the same view at different wavelengths (488 nm, overlay of 488 nm and blank control, blank control), the inventors discovered that most of the target cells expressed green fluorescence, which proved that FITC-labeled short peptide P01 had successfully penetrated target cells and specifically inhibited cell proliferation of KG1α cells. Therefore, the short peptide P01 possessed the potential of being developed into new drugs treating EPS8 positive tumors.

Figure 8:
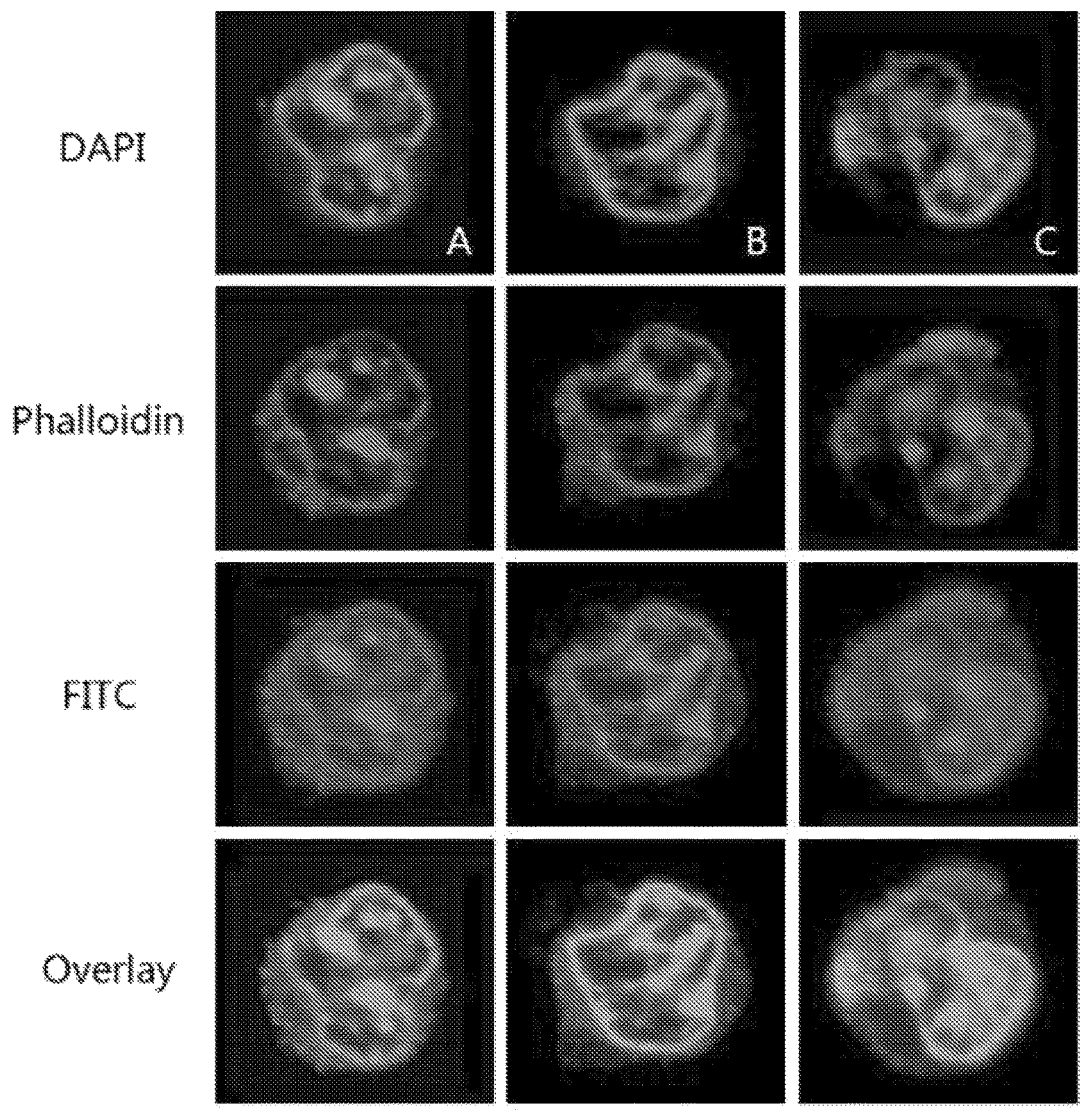
FIG. 8 shows the transmembrane effect of FITC-labeled P01 with laser scanning confocal microscope at wavelengths of 340 nm, 515 nm and 488 nm according to Example 6, A,B,C shows different views.

Example 6 Transmembrane Effect of FITC-Labeled Short Peptide P01 with Laser Scanning Confocal Microscopy KG1α cells were seeded in 6-well plates at $2\times10^5$ cells/well and 1 mL/well. Medium culture was RPMI-1640 containing 10% FBS, 8 hours later, FITC-labeled short peptide P01 was added at the final concentration of 2000 μg/mL. KG1α cells were stained with DAPI (binding with cell nucleus DNA and producing blue fluorescence at the wavelength of 340 nm) and rhodamine-labeled phalloidin (binding with actin and producing red fluorescence at the wavelength of 515 nm). Short peptide P01 was labeled with FITC (producing green fluorescence at the wavelength of 488 nm). 24 hours later, transmembrane effect of FITC-labeled short peptide P01 was observed with laser scanning confocal microscope (FIG. 8). Results showed that at the wavelength of 340 nm, strong blue fluorescence was visible in cell nucleus, clearly demonstrating the cell nucleus outline; at the wavelength of 515 nm, red fluorescence was visible along processes in the cytoplasm, showing the cell skeleton; at the wavelength of 488 nm, green fluorescence was densely distributed in the cytoplasm, presenting distribution of P01. In view of the overlay, fewer and weaker green fluorescence was visible in the cell nucleus than in the cytoplasm, and was unevenly distributed in the cell nucleus. Consequently, these results showed that FITC-labeled short peptide P01 possessed both the ability to penetrate the target cell membrane and also certain ability to penetrate the target cell nucleus membrane.

Taken together, the following conclusions can be drawn: the present invention designed and synthesized a short peptide P01 targeting EPS8 binding with EGFR, and detected its anti-proliferation activity against EPS8 overexpression tumor cell lines KG1α and MCF-7. $IC_{50}$ were 335.6 μg/mL (72 h) and 304.7 μg/mL (72 hours), and the short peptide P01 possessed the potency of being developed into new peptide inhibitors treating EPS8 positive tumors. Furthermore, the short peptide P01 was labeled with FITC, and its transmembrane effect was confirmed with inverted fluorescence microscopy and laser-scanning confocal microscopy. EPS8 is widely expressed in different stages and types of tumor cells and/or tissues, whereas lower or not expressed in normal tissues and cells. Therefore, the new short peptide targeting EPS8 binding with EGFR can be utilized as an active ingredient, and can also be combined with pharmaceutically-acceptable carrier forming compositions. By blocking interaction between EPS8 and EGFR, it is promising to treat EPS8-positive tumor diseases and has the potential to be developed into anti-cancer peptide inhibitor drugs.

While several examples of the present invention are illustrated above and described in detail, however, they cannot be regarded as restricting the scope of present invention. It should be noted that without departure from the concept of the present invention, several variations and modifications may be proposed, and they also belong to the protection domain of the present invention. Therefore, protection domain of the present invention are subject to appended claims.

What is claimed is:

1. A short peptide targeting EPS8 binding with EGFR, wherein the sequence of the peptide is SEQ ID NO: 1, N'-Arg-Lys-Lys-Asn-Lys-Pro-Pro-Pro-Pro-Lys-Lys-C'.

2. The short peptide according to claim 1, wherein the carboxyl of the Lysine on the C' terminus is amidated.

3. The short peptide according to claim 1, wherein the short peptide can block interaction between EPS8 and EGFR.

4. A pharmaceutical composition, comprising the short peptide of claim 1.

5. The pharmaceutical composition according to claim 4, further comprising pharmaceutically applicable excipients.

6. The pharmaceutical composition according to claim 4, in the form of an injection, tablet, capsule, aerosol, suppository, film, controlled release agent, sustained release agent or nano formulation.

7. A method of treating EPS8 positive tumors, comprising: administering a pharmaceutical composition comprising the short peptide of claim 1 to a patient in need thereof.

8. The method according to claim 7, wherein the EPS8 positive tumors are limited to cervical cancer, colorectal cancer, pituitary tumor, oral squamous cell carcinoma, pancreatic ductal cancer, breast cancer, thyroid cancer, esophageal cancer, glioblastoma, multiple myeloma, lymphoma, acute myeloid leukemia, mixed lineage leukemia or acute lymphoid leukemia.

9. The short peptide according to claim 2, wherein the short peptide can block interaction between EPS8 and EGFR.

10. A pharmaceutical composition, comprising the short peptide of claim 2.

11. A method of treating EPS8 positive tumors, comprising:
   administering a pharmaceutical composition comprising the short peptide of claim 2 to a patient in need thereof.

* * * * *